United States Patent
Goldfine

(10) Patent No.: US 7,891,019 B2
(45) Date of Patent: Feb. 22, 2011

(54) HEATED GARMENT

(76) Inventor: Andrew A. Goldfine, 1739 E. 2$^{nd}$ St., Duluth, MN (US) 55812

( * ) Notice: Subject to any disclaimer, the term of this patent is extended or adjusted under 35 U.S.C. 154(b) by 1070 days.

(21) Appl. No.: 11/252,537

(22) Filed: Oct. 18, 2005

(65) Prior Publication Data

US 2006/0080756 A1 Apr. 20, 2006

Related U.S. Application Data

(60) Provisional application No. 60/620,028, filed on Oct. 19, 2004.

(51) Int. Cl.
*A41D 13/00* (2006.01)
(52) U.S. Cl. .......................................................... 2/69
(58) Field of Classification Search .................. 2/455, 2/456, 463–465, 69, 69.5, 92, 102, 108, DIG. 3; 441/87, 88, 102, 106, 108
See application file for complete search history.

(56) References Cited

U.S. PATENT DOCUMENTS

| | | | |
|---|---|---|---|
| 4,355,632 A * | 10/1982 | Sandman | 601/152 |
| 4,702,235 A * | 10/1987 | Hong | 602/13 |
| 5,032,705 A | 7/1991 | Batcheller et al. | 219/211 |
| 5,148,002 A | 9/1992 | Kuo et al. | 219/211 |
| 5,603,648 A * | 2/1997 | Kea | 441/106 |
| 6,439,942 B1 * | 8/2002 | Pillai et al. | 441/106 |
| 6,757,916 B2 * | 7/2004 | Mah et al. | 2/456 |
| 6,910,229 B2 * | 6/2005 | Raithel et al. | 2/456 |

* cited by examiner

*Primary Examiner*—Tejash Patel
(74) *Attorney, Agent, or Firm*—Thomas J. Nikolai; Nikolai & Mersereau, P.A.

(57) ABSTRACT

A heatable garment having a plurality of layers is shown. The first layer is an outer fabric layer of any fabric which is lightweight, durable and treatable and may also be air impervious. Cooperating with the outer fabric layer is an envelope or inflatable bladder having a plurality of interconnected chambers. A further inner layer adjacent the envelope or bladder is a heat producing element such as a plurality of imbedded heating wires woven into a supporting fabric. The supporting fabric may, however, comprise the inner wall of the inflatable envelope. A source of heat energy, such as a battery, is connected to the heat producing element to heat the inner fabric liner. Inflation of the inflatable bladder urges the heat producing element into intimate contact with the body of the wearer. The inflatable bladder also form fits the garment on the body of the wearer and provides insulation against heat loss.

35 Claims, 6 Drawing Sheets

HEATED GARMENT

BACKGROUND OF THE INVENTION

1. Field of the Invention

This invention relates generally to an electrically heated outdoor garment, and more particularly, to an electrically heated outdoor garment with an inflatable bladder for bringing the heating element into intimate contact with the body of the wearer.

2. Description of the Prior Art

Electrically heated garments are known in the prior art. They are useful in combating the effects of cold temperatures when the wearer is subject to prolonged exposure to the elements. Motorcycle riders, in the spring and fall, are particularly exposed to cold winds which make the ride substantially less enjoyable. The prior art heated garments fail to balance fashion, comfort and function.

For example, U.S. Pat. No. 5,032,705 issued to Batcheller et al for an "Electrically Heated Garment" does not allow the wearer to control the closeness of the heating element to the part of the body on which the garment is worn. In the Batcheller et al '705 patent, a lightweight, stretchable garment is provided and a plurality of flexible electrical heating elements are stitched into the garment thus heating the garment. The problem with the garment described in the Batcheller et al '705 patent is that when on a motorcycle, snowmobile, ATV or the like, jackets may flap in the wind and portions of the garment may not be in closet contact with the wearer's body. The resulting air gap acts as a heat barrier. Thus, large portions of the body may remain unheated. Likewise, the insulation provided by the Batcheller et al '705 patent is only as good as the material selected. Heated garments of the like described in the Batcheller et al '705 patent are thus of little use to the rider. They do not provide sufficient insulation to prevent heat loss, and the heating members do not fit snugly yet comfortably into intimate contact with the wearer's body.

U.S. Pat. No. 5,148,002 issued to Kuo et al for a "Multi-functional Garment System" includes an outer shell garment, a detachable inflatable insulation module and a detachable heating module. For the motorcycle enthusiast, the Kuo et al '002 patent is marginally more useful than the garment described in the Batcheller et al '705 patent. The detachable inflatable insulation module provides additional thermal insulation to the wearer. The Kuo et al '002 patent also teaches using an electrical heating module, but does not teach using the insulation module to bring the heating module into intimate contact with the body of the wearer. Thus, the garment does not efficiently warm the user when the wind chill created by high speed driving drops below 50° F.

The prior art therefore does not provide a heated garment which properly balances comfort and function. What is needed is a heated garment which blocks drafts during high speed motorcycle, snowmobile or ATV riding, heats the entire garment, provides a close, comfortable fit thereof and which will warm the entire body or selected parts.

SUMMARY OF THE INVENTION

The present invention meets the needs presented above by providing an article of clothing having in sequence an outer shell, an inflatable layer adjacent the outer shell and a member providing heat energy, where the inflation of the inflatable layer can be used to control the spacing between the member providing heat energy and the wearer's body.

Still yet another object of the present invention is to block drafts when the wearer is using the heated article of clothing while riding on a motorcycle, ATV, snowmobile or the like.

Still yet another object of the present invention is to provide an article of clothing which provides a close fit for riding while at the same time providing a comfortable fit for general wear.

Yet another object of the present invention is to provide a heated article of clothing which can be connected to a variety of electrical current sources for powering a heat energy producing layer.

To this end, the present invention generally comprises an outer layer of fabric which is lightweight, durable and treatable. For example, the outer fabric may form an article of clothing, such as a vest, a jacket, pants, chaps, gloves and the like. The article of clothing is generally fitted to conform to the portion of the body to be protected and to different body sizes and may include at least one pocket for holding an air inlet tube.

The present invention further includes an inflatable bladder corresponding in shape to the outer fabric and disposed within the outer fabric layer. The inflatable bladder comprises a sealed envelope of air-impermeable material and an air inlet tube and a one-way valve for inflating and deflating the envelope. The inflatable bladder may also include a plurality of interconnected chambers. Moreover, the outer fabric layer may be air impermeable and comprise a wall of the bladder.

The present invention also includes a heat energy producing layer located on the opposite side of the inflatable bladder from the fabric layer. The heat energy producing layer may comprise a resistance wire of a predetermined ohmic value connected to an electrical current source. Alternatively, it may comprise a conductive polymer cut to conform to the shape of the garment. An optional innermost fabric layer may be provided for lining the article of clothing. The arrangement is such that when the inflatable bladder is inflated, it urges the heat energy producing layer (and the innermost fabric lining, if one is used) against the body of the wearer. Thus, the inflation of the bladder snugly conforms the heat energy producing member to the body of the wearer, bringing the heating layer into intimate contact with the wearer for improved thermal transfer.

DESCRIPTION OF THE DRAWINGS

Various other features and advantages of the invention will become apparent to those skilled in the art from the following detailed description of the preferred embodiment, especially when considered in conjunction with the accompanying drawings in which like numerals in the several views refer to corresponding parts.

DESCRIPTION OF THE PREFERRED EMBODIMENT

Figure 1:
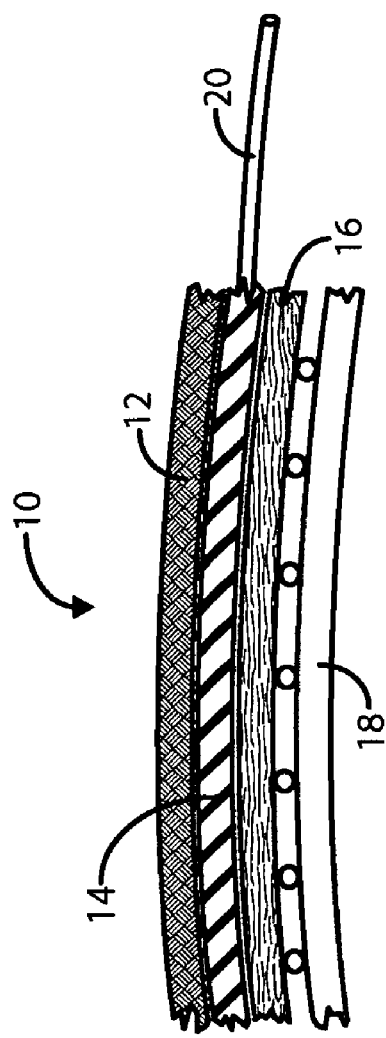
FIG. 1 is a partial cross-sectional view showing a preferred construction of the heated garment of the present invention wherein the inflatable bladder is deflated but the garment is in intimate contact with the skin of a wearer.

As shown in FIG. 1, the present invention comprises a multilayered heated garment 10. The multilayered heated garment 10 has an outer fabric layer 12, an inflatable layer 14 adjacent the fabric layer 12, followed by a heat energy-emitting layer 16 and an optional innermost fabric liner 18. As mentioned, the garment may be a vest, a jacket, pants, chaps or gloves.

Figure 2:
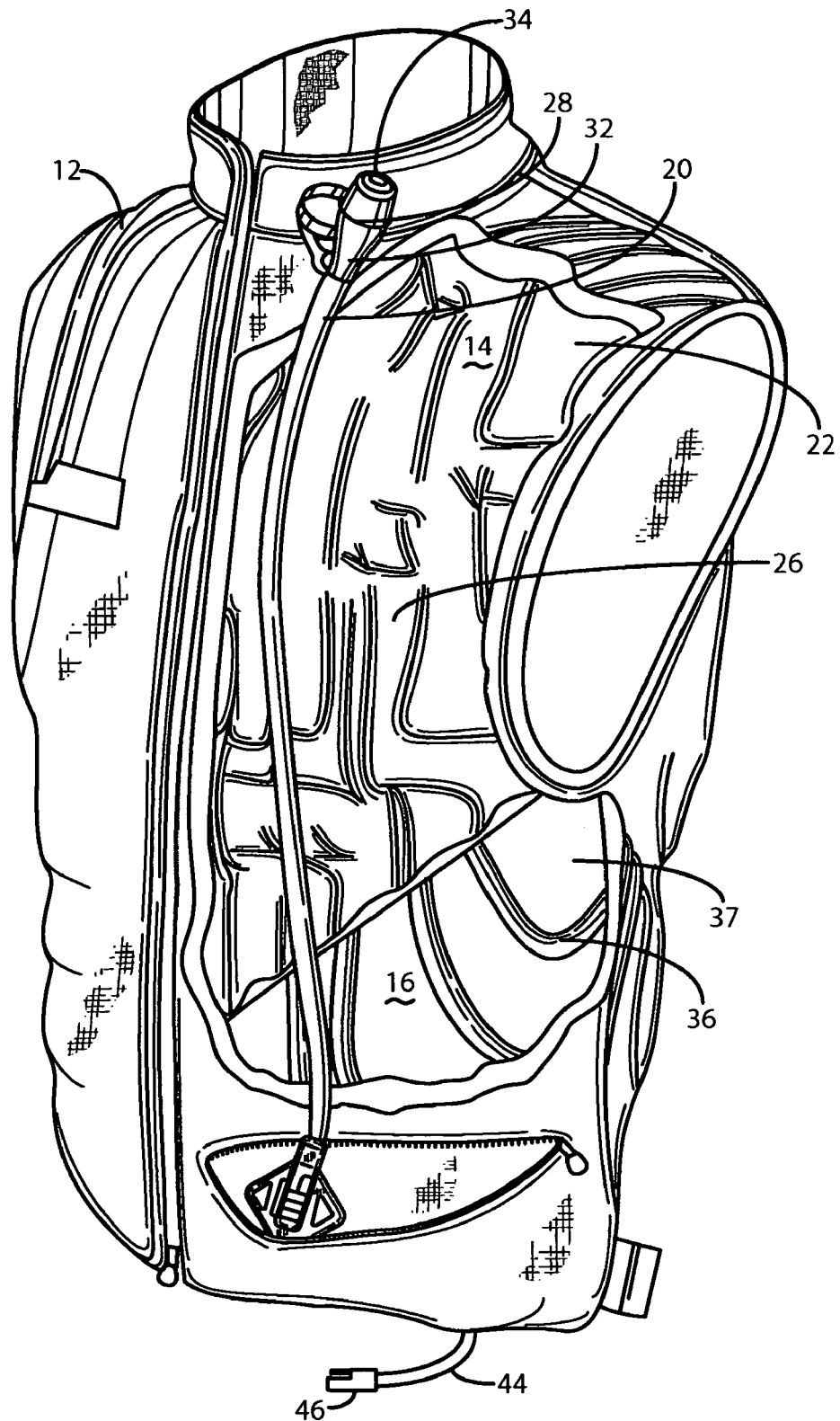
FIG. 2 is a broken-away view of a vest garment incorporating the present invention with the second and third layer in phantom.

FIG. 2 shows a preferred embodiment in which the garment layer 12 is cut to form a sleeveless vest. The outer fabric layer 12 can be manufactured from any number of fabrics which are lightweight, durable and treatable. Such fabric could be leather, fleece, cotton, nylon, Gortex® or the like. Moreover, the outer fabric layer 12 can be manufactured in different sizes to fit or conform to any number of human torsos. In the preferred embodiment shown in FIG. 2, there is at least one pocket 19 for holding an air inlet tube 20 which will be discussed in further detail below.

The inflatable layer 14 generally comprises an inflatable bladder 22. The inflatable bladder 22 is made of an inflatable envelope of an inside and an outside layer of air impermeable material which are sealed together along the edges and elsewhere to form interconnected inflatable pouch-like compartments, as at 26. Those skilled in the art can appreciate that the outer layer 12 can form one wall of the inflatable bladder if made of an air impermeable material. There is an air inlet valve 28 sealably connected to the inflatable envelope 22 at opening 30. It is shown as located so that the tube 20 is in reach of the wearer's mouth. In the preferred embodiment, the user can inflate the bladder 22 by blowing into opening 32 of the air inlet valve 28. Air can also be put into the inflatable bladder 22 using a mechanically compressed air supply or other pneumatic tools. To prevent air loss, cap 34 is provided which covers and seals the inlet 32.

The heatable layer 16, if electric, requires a power source and a resistance heating apparatus. The power source can be any suitable source of electrical current including batteries, portable generators or the like, which provide adequate voltages. Likewise, heating methods may also vary. The heating apparatus may include electrical resistance panels, electro-conductive textiles, or electrical resistance wires woven into a piece of fabric. The heatable layer may also comprise a second wall of the inflatable envelope 22. The heatable layer or element 16 may also include an apparatus for controlling temperature. Such apparatuses may include resistance rheostats, on/off toggle switches, a switch with multiple positions and diodes, or a digital control system.

Figure 3:
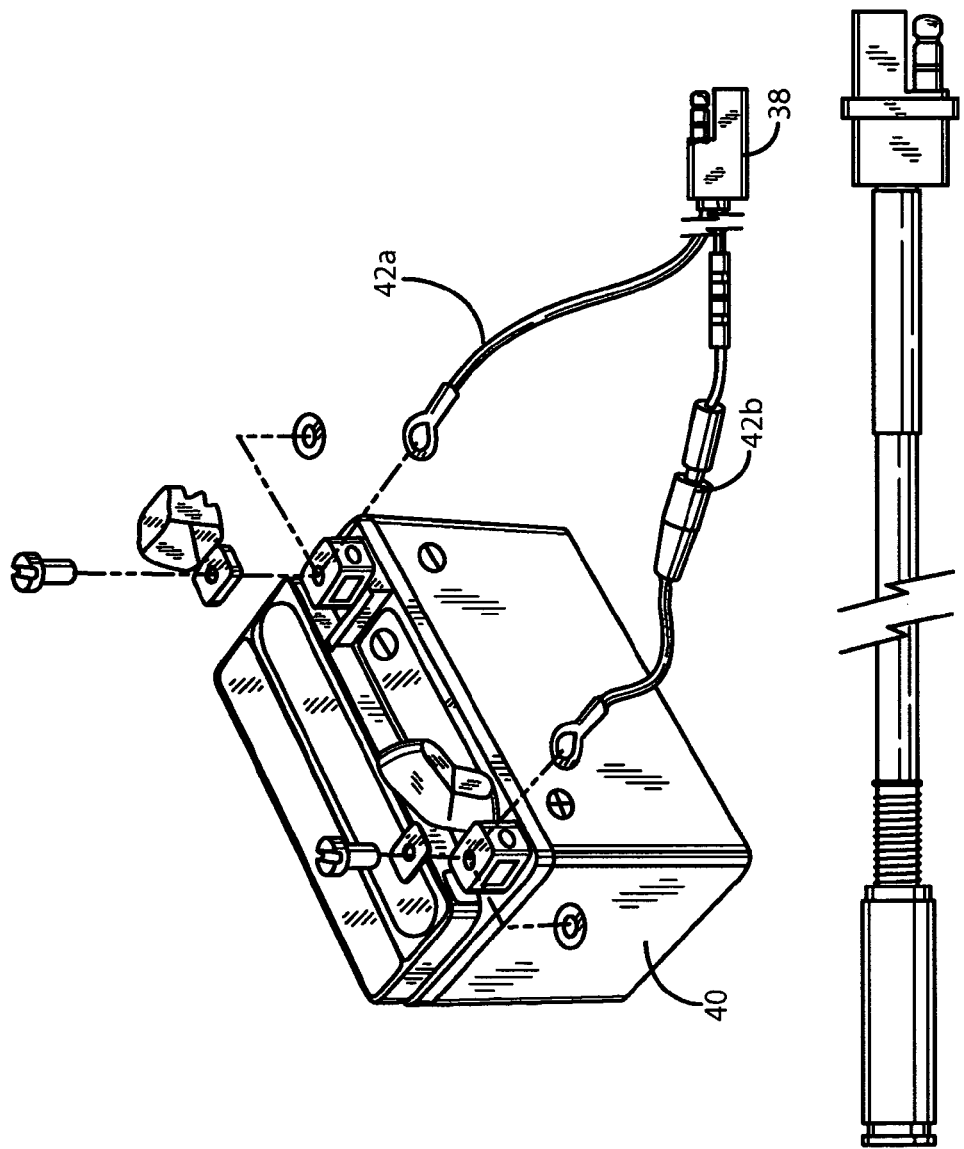
FIG. 3 is a circuit diagram illustrating a preferred way of connecting the heatable garment to a DC source.

As shown in FIG. 3, in the preferred embodiment, the electrical current source 40 may be a vehicle battery typically found in motorcycles, all terrain vehicles, snowmobiles and the like. The electrical current source 40 is connected by insulated wires 42a and 42b to a first electrical plug 38. A power cord 44 (FIG. 2) is connected at one end to the heatable layer 16 and to a second electrical plug 46 at the other. When the first and second electrical plugs 38 and 46 are mated, a series electrical circuit is completed from the current source 40, through wires 42a and 42b and the power cord 44 to the heating apparatus of the heating layer 16. In the preferred embodiment, the heating apparatus may comprise a plurality of resistance wires 36 woven into polymer fabric 37. The resistance wires 36 are coupled to the power cord 44, such that when the series circuit is complete, the electrical current warms the polymer fabric 37.

In one alternative embodiment, the heatable layer may be a conductive, woven polymer sold under the trademark "Gorix®", which itself is capable of becoming heated when an electrical current is made to flow through the fabric. Those interested in gaining a greater understanding of the manner in which Gorix® fabric is produced may refer to the Gordon et al U.S. Pat. No. 6,172,344 which is assigned to Gorix Limited of Great Britain.

Figure 4:
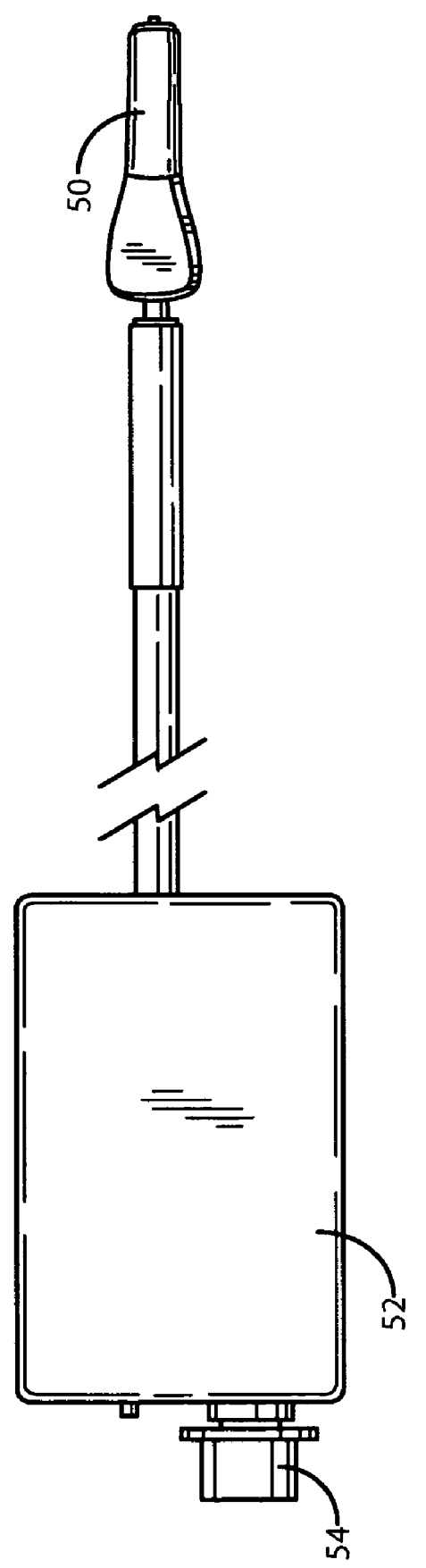
FIG. 4 is a view of a power cord incorporating a thermostat for regulating the flow of current to the heating element.
Figure 5:
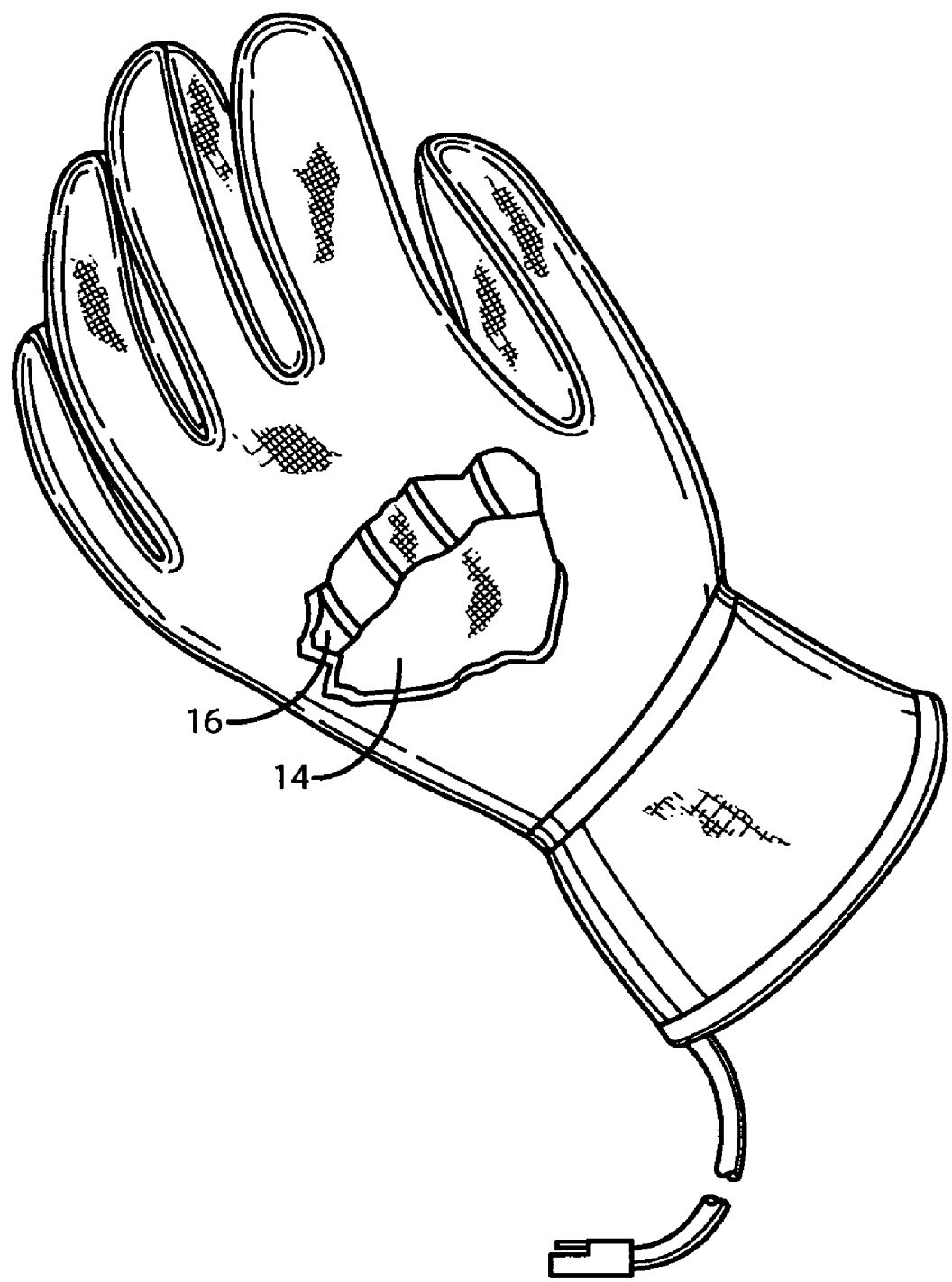
FIG. 5 is a broken-away view of a sock garment incorporating the present invention with the second and third layer in phantom.
Figure 6:
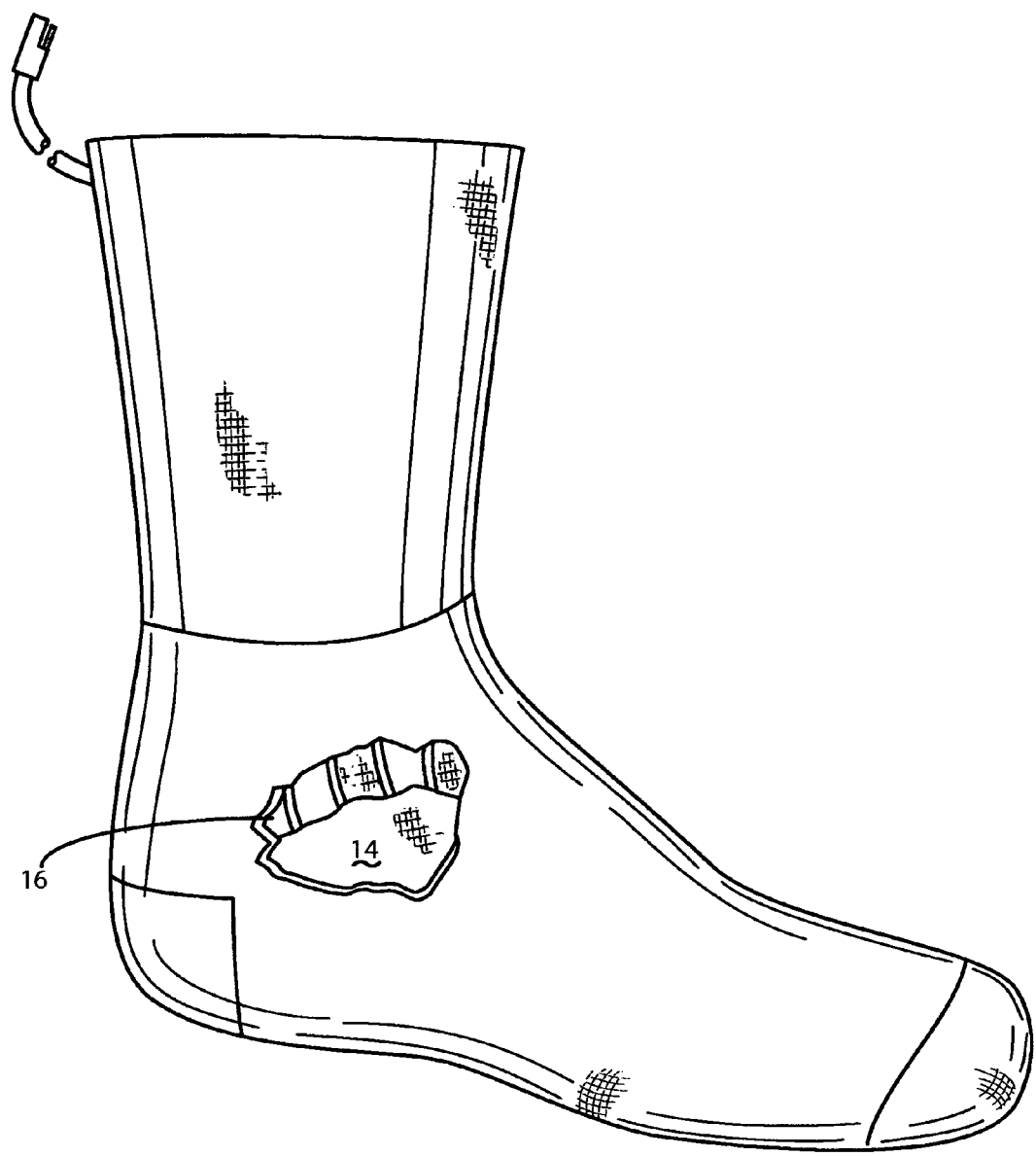
FIG. 6 is a broken-away view of a glove incorporating the present invention with the second and third layer in phantom.

In yet another embodiment, shown in FIG. 4, instead of having a plug, the power cord 44 is adapted to mate with a cigarette lighter plug 50. When the lighter plug 50 is inserted into a cigarette lighter socket in a vehicle, the circuit is completed and electrical current is drawn to the heating apparatus.

In an alternative embodiment the temperature control apparatus may comprise a thermostat 52 of a type commonly used in heating pads, electric blankets and the like. The thermostat 52 allows constant, regulated heat by controlling the amount of current delivered to the heat energy producing layer 16. A rheostat 54 may be used to control the current, increasing the heat as the rheostat 54 is rotated clockwise. LEDs (not shown) are preferably coupled to the thermostat 52 to visually indicate the heat setting.

As shown in FIGS. 1 and 2, the body of the wearer is proximate the optional inner layer 18. As air is introduced into the bladder through tube 20, it urges the heating layer 16 towards the inner lining causing the heating layer to press against the wearer's shirt and body. This, in turn, keeps the wearer's trunk warm and more blood to circulate to the wearer's extremities resulting in greater comfort.

The invention has been described herein in considerable detail and in order to comply with the patent statutes and to provide those skilled in the art with the information needed to apply the novel principles and to construct and use such specialized components as are required. However, it is to be understood that the invention can be carried out by specifically different equipment and devices and that various modifications, both as to equipment and operating procedures, can be accomplished without departing from the scope of the invention itself. For example, and without limitation the heat producing layer may comprise a chemical device capable of producing an exothermic reaction when activated. Hence, the scope of the invention is to be determined from the following claims.

What is claimed is:

1. An article of clothing comprising:
   a) a layered construction fitted to conform to a predetermined portion of an animal body, the layered construction comprising:
   i) an outer fabric layer;
   ii) a first inner layer adjacent the outer fabric layer, said first inner layer being inflatable;
   iii) a second inner layer adjacent the first inner layer, the second inner layer comprising a heat producing element and wherein the inflatable layer, when inflated, urges the heat producing element into more intimate contact with the predetermined portion of the animal body, said heat producing element includes electrical resistance panels in electrical communication with an electrical current source powering the electrical resistance panel; and
   iv) an innermost fabric liner adapted to be closest to the animal body when the article is being worn.

2. The article of clothing of claim 1 wherein said article is fitted to conform to a torso of the animal body.

3. The article of clothing of claim 1 and further including an electrical lead for coupling the electrical current source to the electrical resistance panels.

4. The article of clothing of claim 2 wherein the article is a vest.

5. The article of clothing of claim 2 wherein the article is a jacket.

6. An article of clothing comprising:
   a) a layered construction fitted to conform to a predetermined portion of an animal body, the layered construction comprising:
      i) an outer air impervious fabric layer;
      ii) an inner air impervious layer joined to the outer layer to from an inflatable envelope; and
      iii) heat energy producing member arranged adjacent the inner layer, such that inflation of the inflatable envelope urges the heat energy producing layer against the body of a wearer, wherein the heat energy producing member is an electrical resistance panel in electrical communication with an electrical power source to provide an electrical current to the electrical resistance panel.

7. The article of clothing of claim 6 wherein said article is fitted to conform to a torso of the animal body.

8. The article of clothing of claim 6 and further including a means for connecting the heat producing element to a vehicle battery.

9. The article of clothing of claim 8 and further including an electrical lead for coupling the vehicle battery to the heat producing element.

10. The article of clothing of claim 7 wherein the article is a vest.

11. The article of clothing of claim 7 wherein the article is a jacket.

12. An article of clothing of a layered construction fitted to conform to a predetermined portion of an animal body, the layered construction comprising:
   a) an outer fabric layer;
   b) a first inner layer adjacent the outer fabric layer, said first inner layer being inflatable;
   c) a second inner layer adjacent the first inner layer wherein said second inner layer is a heatable layer that includes electrical resistance panels adapted to be connected to a power source of electrical current; and
   d) an innermost fabric liner adapted to be closest to the animal body when the article is being worn, wherein when the first layer is inflated, the first layer urges the electrical resistance panel into more intimate contact with the predetermined portion of the animal body.

13. The article of clothing of claim 12 wherein said article is fitted to conform to the torso of the animal body.

14. The article of clothing of claim 12 and further including an electric lead coupling the power source to the electrical resistance panel.

15. An article of clothing of a layered construction fitted to conform to a predetermined portion of an animal body, the layered construction comprising:
   a) an outer fabric layer;
   b) a first inner layer adjacent the outer fabric layer, said first inner layer being inflatable;
   c) a heatable layer constructed of a conductive, woven polymer capable of becoming heated when an electrical current is made to flow through the fabric, a source of an electrical current coupled to said conductive woven polymer by an electrical lead;
   d) the inflatable layer, when inflated, urges the heatable layer in more intimate contact with the predetermined portion of the animal body; and
   e) an innermost fabric liner adapted to be closest to the animal body when the article is being worn.

16. The article of clothing of claim 15 wherein said article is fitted to conform to the torso of the animal body.

17. The article of clothing of claim 15 wherein the article is a vest.

18. The article of clothing of claim 15 wherein the article is a jacket.

19. An article of clothing of a layered construction fitted to conform to a predetermined portion of an animal body, the layered construction comprising:
   a) an outer fabric layer;
   b) an inflatable layer adjacent to the outer fabric layer, the inflatable layer made of an envelope of air impermeable material sealed together along its edges, an air inlet valve sealably connected to the envelope at an opening; and
   c) a heatable layer including a power source of electrical current, a heating member coupled to said power source and a temperature controlling apparatus for controlling the temperature of the heating apparatus, wherein when the inflatable layer is inflated, said inflatable layer urges the heating layer in intimate contact with the predetermined portion of the animal body.

20. The article of clothing of claim 19 wherein said article is fitted to conform to a torso of the animal body.

21. The article of clothing of claim 19 wherein the article is a vest.

22. The article of clothing of claim 19 wherein the article is a jacket.

23. The article of clothing of claim 19 wherein the power source is a battery.

24. The article of clothing of claim 19 wherein the power source is a portable generator.

25. The article of clothing of claim 19 wherein the heating apparatus is an electrical resistance panel.

26. The article of clothing of claim 19 wherein the heating apparatus is an electro-conductive textile.

27. The article of clothing of claim 19 wherein the heating apparatus is an electrical resistance wire woven into a fabric.

28. The article of clothing of claim 19 wherein the heating apparatus is a conductive woven polymer.

29. The article of clothing of claim 19 wherein the temperature control apparatus is a resistance rheostat.

30. The article of clothing of claim 19 wherein the temperature control apparatus is a toggle switch capable of turning the power source on and off.

31. The article of clothing of claim 19 wherein the temperature control apparatus is a digital control.

32. The article of clothing of claim 19 wherein the temperature control apparatus is a switch with multiple positions and diodes.

33. The article of clothing of claim 19 wherein the temperature control apparatus comprises a thermostat allowing constant, regulated heat by controlling the amount of current delivered to the heating apparatus.

34. The article of clothing of claim 33 wherein a rheostat is used to control the current, increasing the heat as the rheostat is rotated in a clockwise direction.

35. The article of clothing of claim 34 and further including light emitting diodes operatively coupled to the thermostat to visually indicate a heat setting.

* * * * *